US009097701B2

(12) United States Patent
Krogh

(10) Patent No.: US 9,097,701 B2
(45) Date of Patent: Aug. 4, 2015

(54) APPARATUS FOR HEMOLYZING A BLOOD SAMPLE AND FOR MEASURING AT LEAST ONE PARAMETER THEREOF

(75) Inventor: Søren Christian Krogh, Stenløse (DK)

(73) Assignee: Radiometer Medical ApS, Bronshoj (DK)

( * ) Notice: Subject to any disclaimer, the term of this patent is extended or adjusted under 35 U.S.C. 154(b) by 445 days.

(21) Appl. No.: 12/503,580

(22) Filed: Jul. 15, 2009

(65) Prior Publication Data
US 2010/0015691 A1 Jan. 21, 2010

(30) Foreign Application Priority Data

Jul. 16, 2008 (DK) .................................. 2008 01005

(51) Int. Cl.
B06B 1/00 (2006.01)
G01N 33/00 (2006.01)
C12N 13/00 (2006.01)
C12M 1/34 (2006.01)
(Continued)

(52) U.S. Cl.
CPC ............ *G01N 33/4925* (2013.01); *G01N 21/31* (2013.01); *G01N 2291/02466* (2013.01)

(58) Field of Classification Search
CPC .. A61B 5/06; A61B 5/14539; A61B 5/14542; A61B 5/1477; A61B 5/1491; B01F 1/0022; B01F 2003/125; B01F 2005/0017; B01F 5/0057; G01N 21/31; G01N 2291/02466; G01N 31/162; G01N 33/4925
USPC ........... 422/73, 128; 435/288.7, 173.7, 173.4; 436/522, 17
See application file for complete search history.

(56) References Cited

U.S. PATENT DOCUMENTS 3,972,614 A * 8/1976 Johansen et al. ................ 356/36
4,764,021 A 8/1988 Eppes
(Continued)

FOREIGN PATENT DOCUMENTS

JP 11-347392 12/1999
JP 2000-005163 1/2000
(Continued)

OTHER PUBLICATIONS

Radiometer Brochure: "The ABL800 FLEX: Setting the Standard," XP002549319, 2006.
(Continued)

*Primary Examiner* — Dean Kwak
(74) *Attorney, Agent, or Firm* — Finnegan, Henderson, Farabow, Garret & Dunner LLP

(57) ABSTRACT

An apparatus for hemolyzing a blood sample and for measuring at least one parameter thereof comprises a sample chamber for accommodation of the blood sample, the sample chamber having a first sidewall and an opposite second sidewall. The apparatus also comprises ultrasonic generator for generating ultrasonic waves in the first and second sidewalls so as to cause the blood sample provided between the first and second sidewall to be hemolyzed. Further, the apparatus comprises an optical measuring device for measuring the at least one parameter in the hemolyzed blood sample when the hemolyzed blood sample is provided between the first and second sidewalls. The ultrasonic generator of the apparatus comprises a first ultrasonic generator for generating ultrasonic waves in the first sidewall and a second ultrasonic generator for generating ultrasonic waves in the second sidewall.

16 Claims, 3 Drawing Sheets

Figure 1:
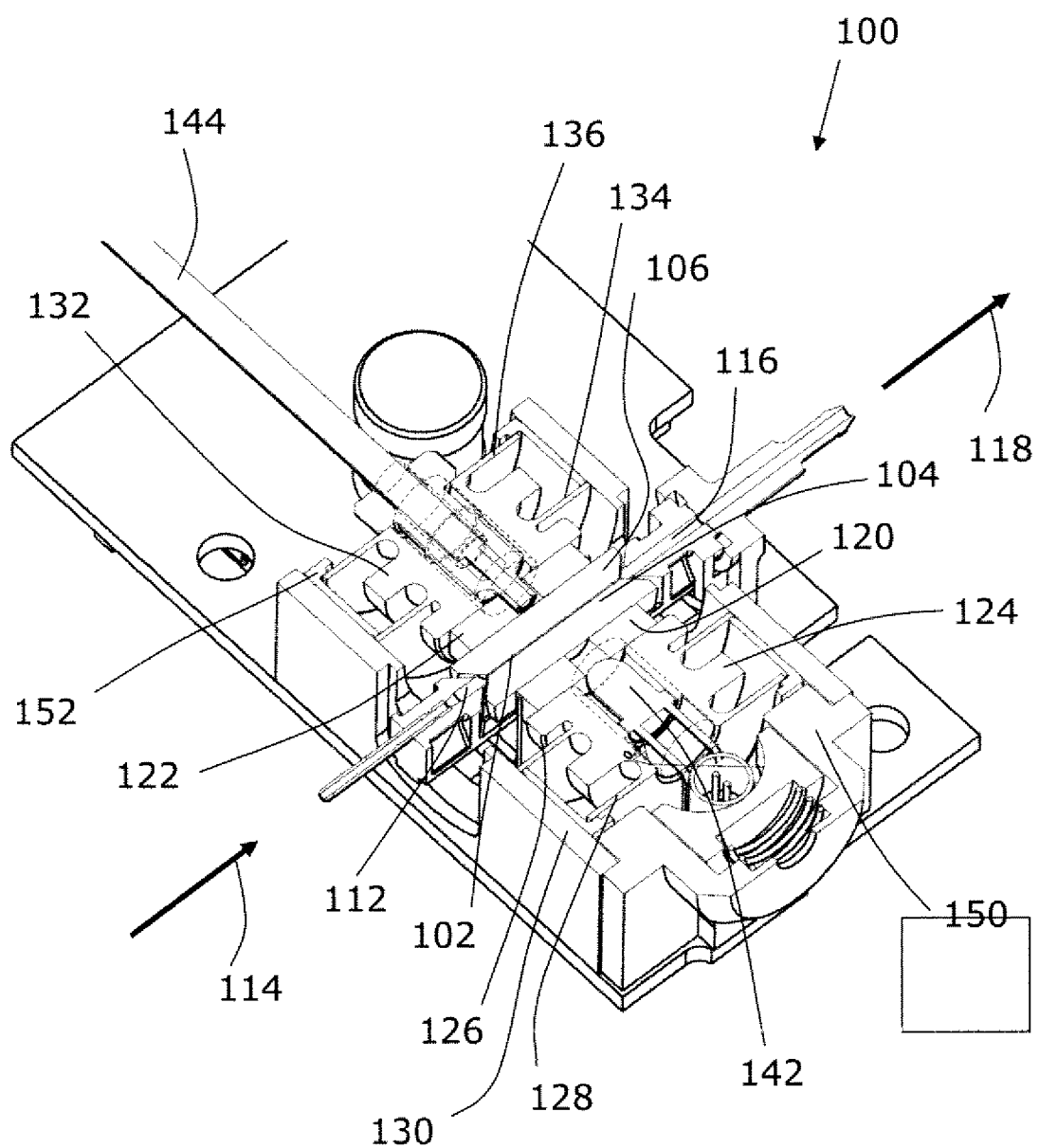

(51) Int. Cl.
*G01N 31/00* (2006.01)
*G01N 33/49* (2006.01)
*G01N 21/31* (2006.01)

(56) References Cited

U.S. PATENT DOCUMENTS

| | | | |
|---|---|---|---|
| 6,100,084 A | 8/2000 | Miles et al. | 435/306.1 |
| 6,244,738 B1 | 6/2001 | Yasuda | |
| 6,506,584 B1 * | 1/2003 | Chandler et al. | 435/173.7 |
| 2003/0066915 A1 | 4/2003 | Taylor | 241/100 |

FOREIGN PATENT DOCUMENTS

| | | |
|---|---|---|
| JP | 2001-296292 | 10/2001 |
| WO | WO 01/0183102 A2 | 8/2001 |
| WO | 2007/083295 A2 | 7/2007 |

OTHER PUBLICATIONS

Translation and Comparison of JP 11-347392 and U.S. Patent No. 6,244,738.

\* cited by examiner

APPARATUS FOR HEMOLYZING A BLOOD SAMPLE AND FOR MEASURING AT LEAST ONE PARAMETER THEREOF

The present invention relates to an apparatus for hemolyzing a blood sample and for measuring at least one parameter thereof, the apparatus comprising: a sample chamber for accommodation of the blood sample, the sample chamber having a first sidewall and an opposite second sidewall; ultrasonic means for generating ultrasonic waves in the first and second sidewalls so as to cause the blood sample provided between the first and second sidewall to be hemolyzed; and optical measuring means for measuring the at least one parameter in the hemolyzed blood sample when the hemolyzed blood sample is provided between the first and second sidewalls.

Hemolyzing a blood sample in order to determine a parameter thereof is known in the art. One such example may be found in U.S. Pat. No. 3,972,614. The apparatus disclosed therein has a housing including a conduit for accommodating the blood sample and one ultrasonic device for generating ultrasonic waves. The conduit includes two opposing window members, the first of which is in contact with the ultrasonic device while the second is in contact with a spring suspended backing member in the shape of an anvil. When the ultrasonic device generates ultrasonic waves in the system, the waves are transferred directly to the first window and indirectly via the housing and the anvil to the other window. Thus, the ultrasonic waves in the second window are not generated directly in the window, but result from the oscillation response of the anvil. This system suffers from the drawback that ultrasonic waves generated from only one side of the sample conduit may give rise to both an uneven propagation of the waves across the conduit as well as uncontrolled oscillations of the conduit. This is due to the fact that it is a difficult task to properly design the anvil to obtain the required oscillation of the anvil and thus of the second window. The uneven propagation and uncontrolled oscillations may result in degradation of the conduit which may eventually leak. Thus, the usable lifetime of the conduit may be essentially reduced. Further, this prior art apparatus is relatively big as the arrangement with only one ultrasonic device requires a relatively large mass of the system to obtain a frequency of oscillation necessary for hemolyzing a blood sample. Reducing the mass of this system will most likely provide a frequency of oscillation being so high that the hemolyzation of the sample becomes insufficient.

The present invention relates to an apparatus of the above mentioned kind, in which apparatus the ultrasonic generator comprises a first ultrasonic generator for generating ultrasonic waves in the first sidewall and a second ultrasonic generator for generating ultrasonic waves in the second sidewall.

One advantage of the present invention is that the apparatus has ultrasonic generators actively generating ultrasonic waves directly in both the first and the second sidewalls of the sample chamber, thereby establishing a very controlled transverse reciprocation of the sidewalls relative to the sample chamber. As the oscillation is controlled from both sidewalls, there is a more limited number of degrees of freedom in the system. Thereby modes of higher orders or unwanted resonances may be avoided and there are fewer components in the system, that have to be designed to provide a specific response relative to a single generation of ultrasonic waves. Further, from a vibration point of view it is desirable to have a very controlled oscillation as it may thus be avoided that the sample chamber is oscillating in a manner that is damageable to the chamber. The generation of ultrasonic waves in one sidewall is essentially independent of the generation of ultrasonic waves in the other sidewall. It cannot be fully avoided that ultrasonic waves generated in one sidewall is transferred to the other sidewall, but the effect of the transferred waves is insignificant relative to the effect of the waves generated directly in the other sidewall. In the apparatus according to the invention, the first and the second ultrasonic generators may be operable independently of each other.

Further, with the apparatus according to the invention it is now possible to make the apparatus very small compared to the apparatus of the prior art.

The chamber for accommodation of the blood sample comprises first and second sidewalls which are arranged substantially parallel, opposite each other, i.e. the two walls face each other. The volume of the chamber may be in the range of 0.1-20 µl, preferably 1 µl. The distance between the first and the second sidewall may be 0.05-0.3 mm, preferably 0.1 mm.

The first and the second sidewalls may be made from a material that is transparent for the radiation emitted from the optical device to the sample. Alternatively, the sidewalls may be made essentially from a non-transparent material, but having one or more areas thereof being transparent for the radiation. The transparent areas may comprise a glass material and/or a plastic material such as polystyrene, PMMA (polymethyl methacrylate), or a cyclic olefin copolymer (COC), preferably Topas from the company Topas Advanced Polymers.

The optical measuring device of the apparatus according to the present invention may be adapted to measure at least one parameter of a blood sample. Preferably, the parameter is selected from the group of so-called oximetry parameters ctHb, $sO_2$, $FO_2Hb$, FCOHb, FMetHb, FHHb, FHbF, ctBil, but also parameters such as $pCO_2$, $pO_2$, cGlu, cUrea, albumin and cholesterol may be determined. Further, the content of diagnostic dyes as well as the content of proteins in the blood of patient may be determined by the optical device of the apparatus. The optical measuring device may be used to determine the content of the parameters before and/or after hemolyzation of the blood sample. Some of the parameters mentioned require the blood sample to be hemolyzed before measurement, others can be measured before, but a more accurate result may be obtained after hemolyzation. Further, for some parameters it may be needed to determine how much content was inside the cells before hemolyzation. This may be determined by measuring the parameter both before and after the hemolyzation as for some parameters the content in the cells may measurable only after hemolyzation. In this case the apparatus may be controlled such that the optical measuring device is operated prior to hemolyzing the blood and subsequent to hemolyzing the blood sample. The optical measuring device comprises an optical emitter for emitting radiation to the sample in the sample chamber and an optical detector for determining the amount of light transmitted through or reflected by the sample. The radiation transmitted in the optical system is preferably in the ultraviolet to infrared area, more preferably in the area of approx. 400-700 nm. The optical emitter is preferably a white LED and the detector a Si detector.

The ultrasonic generator may be arranged abutting the sidewalls of the sample chamber. Alternatively, the second ultrasonic generator may form part of the sidewalls.

Preferably, the first and second ultrasonic generators are adapted to be operated in phase. The first and second ultrasonic generators may be adapted to be operated concurrently or independently of each other. In the context of the present invention the term "in phase" shall be understood such that the activation of the first and the second ultrasonic generators result in the first and second sidewalls oscillating at the same frequency, which their zero and maximum value occurring simultaneously. In order to obtain the most efficient hemolyzation it is further preferred that when reciprocating, the sidewalls move in opposite directions, either towards each other or away from each other. Preferably, the ultrasonic generator is operated to obtain a frequency of oscillation in the system in the area 20-100 kHz, more preferably at 30 kHz which is a frequency area shown to be efficient for hemolyzing a blood sample.

In one embodiment, the ultrasonic generator comprises a first and a second piezoelectric element connected to the first and second sidewall, respectively. Use of a piezoelectric element has the advantage that it makes the activation of the ultrasonic generator very controllable. Further, piezoelectric elements are relatively inexpensive and are very efficient. The piezoelectric elements for use with the apparatus according to the invention preferably provide a large movement relative to the potential applied.

In another embodiment, the first ultrasonic generator comprises a first electrode in contact with the first sidewall and the second ultrasonic generator comprises a second electrode in contact with the second sidewall, an alternating current being applied to the first and the second electrodes for generating ultrasonic waves in the sidewalls. When the two electrodes are connected by an AC voltage generator, the voltage applied over the electrodes result in the sidewalls reciprocating. The oscillation frequency of the sidewalls will be determined by the frequency of the potential applied over the electrodes and the oscillation amplitude will be determined by the potential.

Preferably, the ultrasonic generators are operated for 1-5 s, more preferred 2 s. When operating the ultrasonic generators some of the energy from the reciprocation of the sidewalls will be transferred as heat to the sample and it should be assured that the operating time is short enough to avoid overheating of the sample which may otherwise lead to denature of the sample.

In a preferred embodiment the first and the second sidewalls and the first and the second ultrasonic generators are symmetrically arranged around the sample chamber. An advantage with this arrangement is that it is much easier to obtain a symmetrical reciprocation of the sidewalls. Take as an example the above mentioned embodiment with the ultrasonic generators comprising two electrodes. When applying a selected AC potential it may be possible to obtain an oscillation of the sidewalls having the sample chamber in the nodal point of the oscillation, thus resulting in the sidewalls reciprocating either towards or away from each other.

The sidewalls of the sample chamber may be made as a one piece element or they may be made from separate elements. In some instances it may be needed to form the sample chamber from a one piece element in order to avoid many production steps; in others it may be advantageous to form the chamber from individual elements, thus being able to choose the different elements from demands to strength, tightness to the surroundings etc.

In order to increase the inertia of the reciprocating mass, the apparatus may comprise a first and a second mass element which are coupled to the first and second ultrasonic generators, respectively. One advantage of increasing the reciprocating mass is that a more uniform reciprocating movement may be achieved. The mass element elements may comprise any material as long as the mass of the elements are adjusted to obtain the required frequency of oscillation of the ultrasonic waves.

In order to obtain a compact system it is preferred that a photometric emitter of the optical system is located in the first mass element and a photometric detector is located in the second mass element.

In a preferred embodiment, the apparatus further comprises a housing accommodating the sample chamber and the first and second ultrasonic generators, wherein each of the first and second mass elements has one or more spring elements elastically securing each mass element to the housing. The spring elements allow the mass elements to reciprocate together with the ultrasonic generators, however limits the movements of the mass elements.

The spring elements may form part of the mass elements. As an example at least one of the mass elements may comprise a spring element in the form of a flange extending from an outer surface of the mass element. One or more of the mass elements may comprise a plurality of spring elements. In one embodiment each of the mass elements comprises two spring elements each being in the form of a flange extending radially from the mass element. By providing at least two spring elements the mass elements may be suspended at two positions e.g. at its two ends relative to the intended direction of reciprocation, thus avoiding movement of the mass elements in other directions. In a preferred embodiment, the suspension via the spring elements in the housing results in the sidewalls of the sample chamber being distorted against each other.

Preferably, the mass element is made of aluminum or beryllium copper and has a weight of 1-10 g, preferably 6 g each.

The accompanying drawings, which are incorporated in and constitute a part of this specification, illustrate embodiments of the invention and together with the description serve to explain the principles of the invention. In the drawings.

Figure 2:
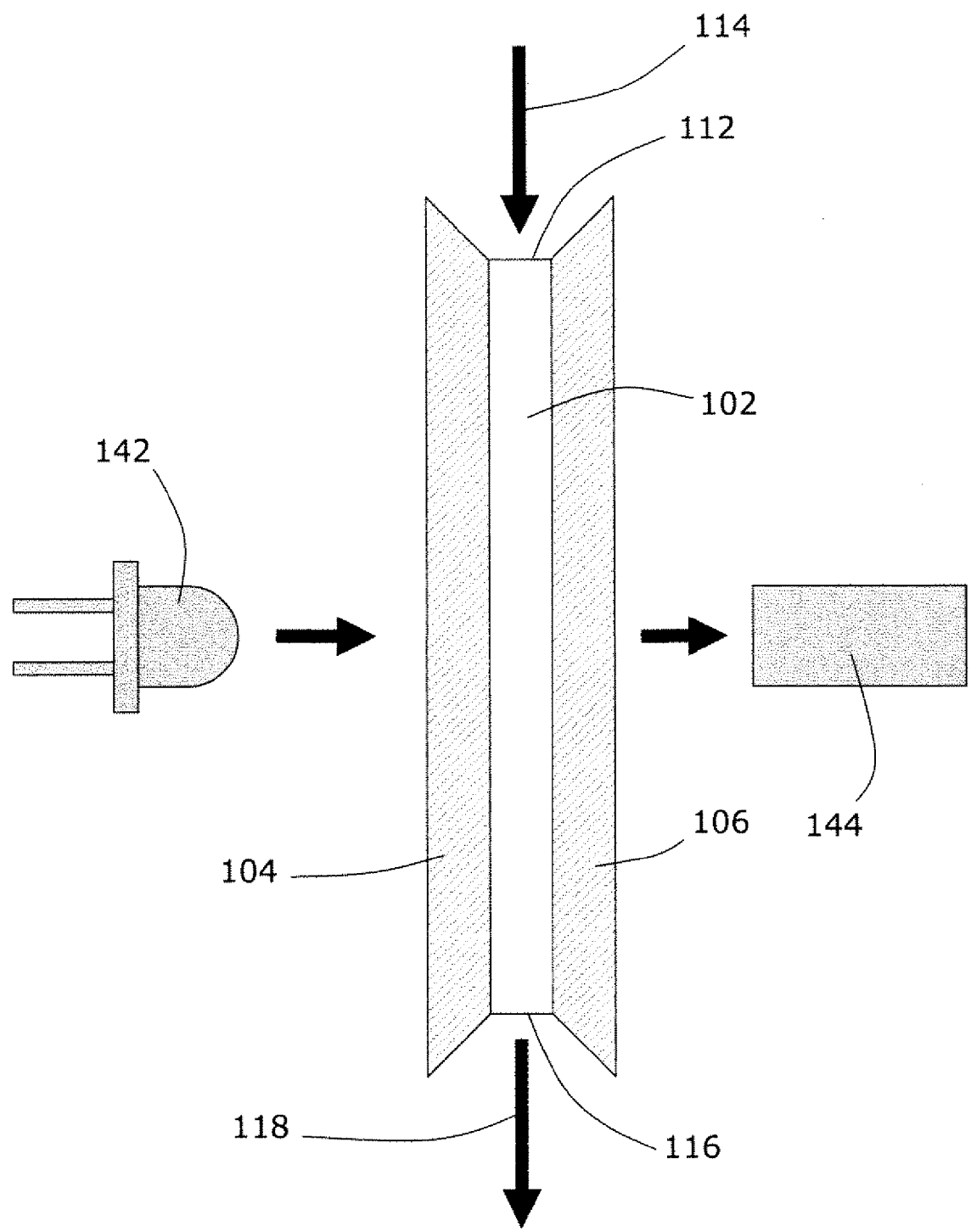
Figure 3:
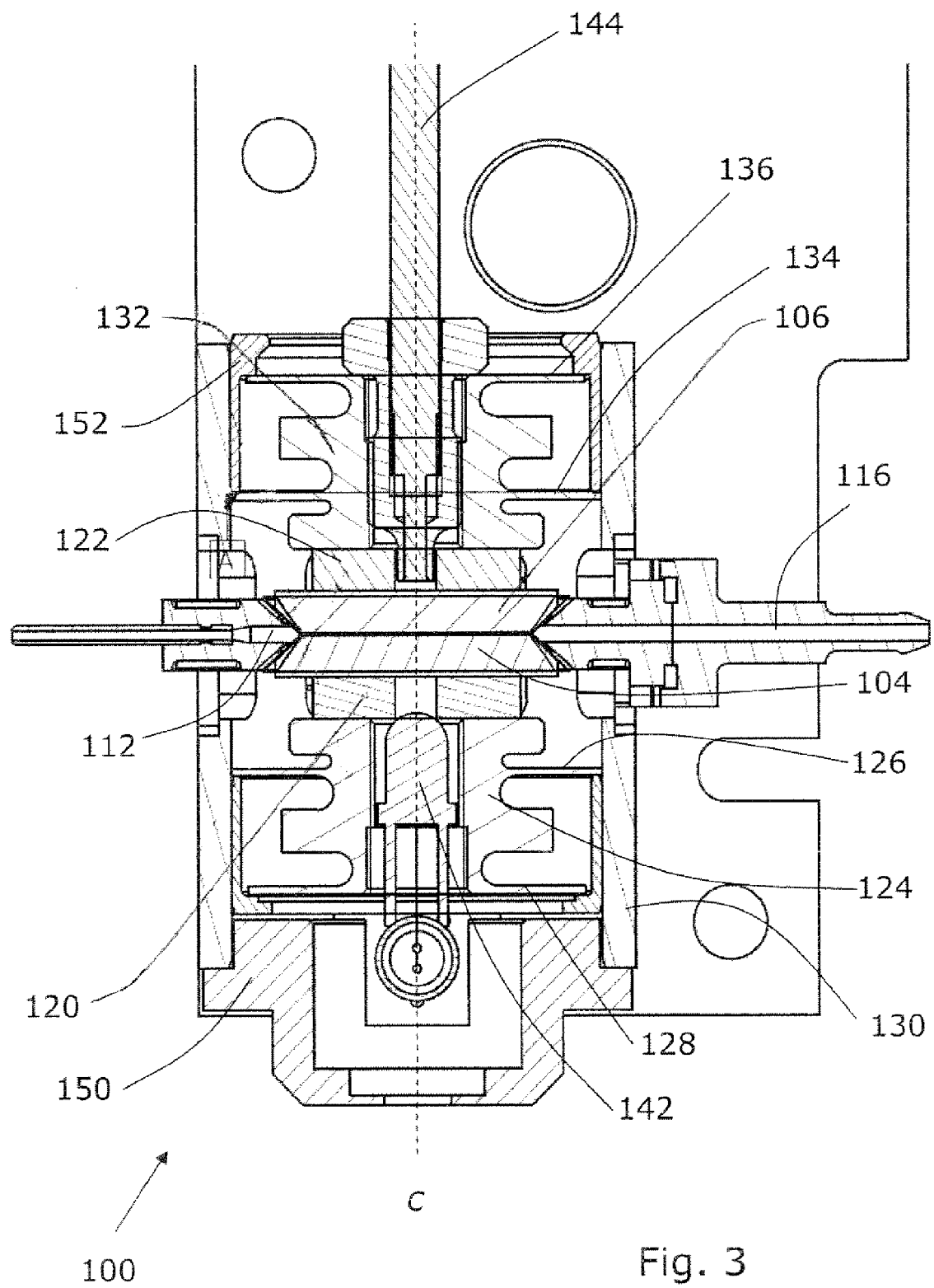

FIG. 1 discloses an isometric illustration of a section of the apparatus according the present invention, FIG. 2 discloses a cross-sectional view of the chamber for accommodation of the blood sample, and FIG. 3 disclose a cross-sectional view of the apparatus according to the present invention.

FIGS. 1 and 3 disclose an apparatus 100 for hemolyzing a blood sample and for measuring at least one parameter thereof. The apparatus 100 is accommodated in a housing 130 closed by end parts 150, 152. The housing is approx. 30 mm long and 20 mm wide. The apparatus 100 comprises a chamber 102 for accommodation of a blood sample, see also FIG. 2. The chamber 102 is defined by a first sidewall 104 and a second sidewall 106, see FIG. 2. Both sidewalls 104, 106 are made of glass and have a thickness of 2 mm. The distance between the sidewalls is approx. 0.1 mm. The chamber 102 comprises an inlet 112 through which the blood sample is transferred into the chamber 102 as indicated by arrow 114. Additionally, the chamber 102 defines an outlet 116 through which a blood sample accommodated in the chamber 102 may be transferred out of the chamber 102 as is indicated by arrow 118. The inlet 112 and the outlet 116 may additionally be used for flushing the chamber 102 so as to clean the chamber after removal of a blood sample. A pump (not shown) may be provided for pumping any sample and other fluids into and from the chamber 102. The sample chamber has a volume of approx. 1 µl.

The apparatus 100 further comprises a first ultrasonic generator 120 and a second ultrasonic generator 122, both in the form of a piezoelectric element, for example. One side of the first ultrasonic generator 120 abuts the first sidewall 104 such that ultrasonic vibrations caused by the first ultrasonic generator 120 is transferred to the first sidewall 104. Correspondingly, the second ultrasonic generator 122 abuts the second sidewall 106 transferring ultrasonic vibrations thereto. It will be appreciated that such vibrations are transferred to a blood sample accommodated in the chamber 102.

On the opposite side of the first ultrasonic generator 120, a first mass element 124 is arranged to abut the first ultrasonic generator 120. Due to the abutment, activation of the first ultrasonic generator 120 causes the first mass element 124 to move. The first mass element 124 is provided to increase the mass which during use of the apparatus reciprocates. The first mass element 124 is suspended by means of a proximal spring element 126 and a distal spring element 128. Each of the spring elements 126,128 are provided in the form of a flange extending radially from the first mass element 124. It will be appreciated that the flange may be a separate element which is attached to the first mass element 124. Alternatively, the flanges 126,128 form part of the first mass element 124. In the latter embodiment, the mass element 124 and the flanges 126,128 may define a monolithic element, i.e. one element without seams in the transition between the flanges 126,128 and the mass element 124.

The flanges 126,128 may be adapted to abut the walls of the housing 130. Due to the accommodation in the housing 130 and the shape of the flanges 126,128, the mass element 124 will primarily move transversely relative to the extension of the sample chamber 120, i.e. along the line c in FIG. 3. Movement in a direction transverse to the line c is substantially prevented, due to the abutment between the flanges 126,128 and the housing 130.

Similar to the first mass element 124, a second mass element 132 is arranged to abut the second ultrasonic generator 122. Again the second mass element 132 comprises a proximal spring element 134 and a distal spring element 136 which force the second mass element 132 into abutment with the second ultrasonic generator 122. Moreover, the proximal spring element 134 and the distal spring element 136 retain the second mass element 132 in the housing 130 of the apparatus 100. Each of the mass elements 124, 132 are made of beryllium copper and has a weight of approx. 6 g.

Each of the mass elements 124,132 define a cavity for accommodation of the measuring device, which in the embodiment of the figures comprises a light emitter 142 and an optical fiber 144 connected to a light detector (not shown). The light emitter 142 is a white LED emitting light having a wavelength in the range of approx. 400-700 nm and the detector is a silicon (Si) detector.

When a measurement of a blood sample is to be performed, the sample is transferred into the sample chamber 102. Then the piezoelectric elements 120, 122 are activated at a frequency of approx. 30 kHz for approx. 2 s. thereby generating oscillation of the sidewalls 104, 106. This oscillation is transferred to the sample in the chamber 102 which is then hemolyzed. After hemolyzation, the light emitter 142 is activated and radiation is transmitted through approx. 0.1 µl of the sample in the sample chamber 102. The radiation is then transmitted via the optical fiber 144 to the detector and the detected signals converted to values representing the content of the requested parameters of the sample.

It will be apparent to those skilled in the art that various modifications and variations can be made in the sensor system and the sampling cell of the present invention without departing from the spirit or scope of the invention. Thus, it is intended that the present invention cover the modifications and variations of this invention provided they come within the scope of the appended claims and their equivalents.

The invention claimed is:

1. An apparatus for hemolyzing a blood sample and for measuring at least one parameter thereof, the apparatus comprising:
    a sample chamber for accommodating the blood sample, the sample chamber having a first sidewall and a second sidewall opposite the first sidewall;
    an ultrasonic means for generating ultrasonic waves in the first sidewall and the second sidewall so as to cause the blood sample provided between the first sidewall and the second sidewall to be hemolyzed; and
    an optical measuring means for measuring the at least one parameter in the hemolyzed blood sample when the hemolyzed blood sample is provided between the first sidewall and the second sidewall,
    wherein the ultrasonic means comprises a first ultrasonic means for generating ultrasonic waves in the first sidewall and a second ultrasonic means for generating ultrasonic waves in the second sidewall, wherein the first sidewall and the second sidewall and the first ultrasonic means and the second ultrasonic means are symmetrically arranged around the sample chamber,
    and wherein a first mass element, which is a separate element from the sample chamber, is coupled to the first ultrasonic means and a second mass element, which is a separate element from the sample chamber, is coupled to the second ultrasonic means.

2. An apparatus according to claim 1, wherein the first ultrasonic means and the second ultrasonic means are adapted to be operated in phase.

3. An apparatus according to claim 1, wherein the first ultrasonic means and the second ultrasonic means each comprise a piezoelectric element.

4. An apparatus according to claim 1, wherein the first ultrasonic means comprises a first electrode in contact with the first sidewall and the second ultrasonic means comprises a second electrode in contact with the second sidewall, an alternating current being applied to the first electrode and the second electrode for generating ultrasonic waves in the first sidewall and the second sidewall.

5. An apparatus according to claim 1, wherein the first sidewall and the first ultrasonic means are symmetrically arranged around the sample chamber relative to the second sidewall and the second ultrasonic means.

6. An apparatus according to claim 1, wherein the first sidewall and the second sidewalk of the sample chamber are individual elements.

7. An apparatus according to claim 1, wherein the first sidewall and the second sidewall of the sample chamber are made as a one piece element.

8. An apparatus according to claim 1, wherein the optical measuring means comprises a photometric light emitter located in the first mass element and a photometric detector located in the second mass element.

9. An apparatus according to claim 1, further comprising a housing accommodating the sample chamber and the first ultrasonic means and the second ultrasonic means, wherein the first mass element and the second mass element each has one or more spring elements elastically securing each mass element to the housing.

10. An apparatus for hemolyzing a blood sample and for measuring at least one parameter thereof the apparatus comprising:
    a sample chamber for accommodating the blood sample, the sample chamber have a first sidewall and a second sidewall opposite the first sidewall;
    a first ultrasonic generator and a second ultrasonic generator for generating ultrasonic waves in the first sidewall and the second sidewall, respectively, so as to cause the blood sample provided between the first sidewall and the second sidewall to be hemolyzed, wherein the first sidewall and the second sidewall and the first ultrasonic generator and the second ultrasonic generator are symmetrically arranged around the sample chamber, and wherein a first mass element, which is separate element from the sample chamber, is coupled to the first ultrasonic generator and a second mass element, which is a separate element from the sample chamber, is coupled to the second ultrasonic generator; and an optical measuring device for measuring the at least one parameter in the hemolyzed blood sample when the hemolyzed blood sample is provided between the first sidewall and the second sidewalls.

11. An apparatus according to claim 10, wherein the first ultrasonic generator and the second ultrasonic generator are adapted to be operated in phase.

12. An apparatus according to claim 10, wherein the first ultrasonic generator and the second ultrasonic generator each comprise a piezoelectric element.

13. An apparatus according to claim 10, wherein the first ultrasonic generator comprises a first electrode in contact with the first sidewall and the second ultrasonic generator comprises a second electrode in contact with the second sidewall, an alternating current being applied to the first electrode and the second electrode for generating ultrasonic waves in the first sidewall and the second sidewall.

14. An apparatus according to claim 10, wherein the first sidewall and first ultrasonic generator are symmetrically arranged around the sample chamber relative to the second sidewall and the second ultrasonic generator.

15. An apparatus according to claim 10, wherein the optical measuring device comprises a photometric light emitter located in the first mass element and a photometric detector located in the second mass element.

16. An apparatus according to claim 10, further comprising a housing accommodating the sample chamber and the first ultrasonic generator and the second ultrasonic generator, wherein the first mass element and the second mass element each has one or more spring elements elastically securing each mass element to the housing.

* * * * *

UNITED STATES PATENT AND TRADEMARK OFFICE
CERTIFICATE OF CORRECTION

| | |
|---|---|
| PATENT NO. | : 9,097,701 B2 |
| APPLICATION NO. | : 12/503580 |
| DATED | : August 4, 2015 |
| INVENTOR(S) | : Søren Christian Krogh |

It is certified that error appears in the above-identified patent and that said Letters Patent is hereby corrected as shown below:

Claims

Claim 6, col. 6, line 45,

"sidewall and the second sidewalk of the sample chamber are" should read

--sidewall and the second sidewall of the sample chamber are--

Claim 10, col. 7, line 16,

"sidewall and the second sidewalls" should read

--sidewall and the second sidewall--

Signed and Sealed this
Nineteenth Day of January, 2016

Michelle K. Lee
*Director of the United States Patent and Trademark Office*